United States Patent [19]

Effland et al.

[11] Patent Number: 5,006,537
[45] Date of Patent: Apr. 9, 1991

[54] 1,3-DIHYDRO-1-(PYRIDINYLAMINO)-2H-INDOL-2-ONES

[75] Inventors: Richard C. Effland, Bridgewater; David G. Wettlaufer, Phillipsburg, both of N.J.

[73] Assignee: Hoechst-Roussel Pharmaceuticals, Inc., Somerville, N.J.

[21] Appl. No.: 388,437

[22] Filed: Aug. 2, 1989

[51] Int. Cl.$^5$ .................. A61K 31/44; C07D 213/74
[52] U.S. Cl. ................... 514/339; 514/278; 514/333; 546/15; 546/17; 546/256; 546/273
[58] Field of Search .................. 546/17, 273, 256; 514/339, 333, 278

[56] References Cited

FOREIGN PATENT DOCUMENTS 0287982 10/1988 European Pat. Off. .

OTHER PUBLICATIONS

Avedeyev, et al., "6-Substituted-1-Heterocyclic Arylamino-3-Arylhydroxyindoles, Khim. Geterotsikl (4) 524–7 (1983).

Primary Examiner—Mary C. Lee
Assistant Examiner—Jacqueline Haley
Attorney, Agent, or Firm—Elliott Korsen

[57] ABSTRACT

This invention relates to 1,3-dihydro-1-(pyridinylamino)-2H-indol-2-ones of the formula

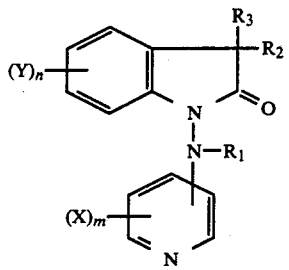

where $R_1, R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl or heteroaryl cycloalkane; X and Y are independently hydrogen, halogen, hydroxy, loweralkyl, loweralkoxy, nitro, amino or trifluoromethyl; m and n are independently integers of 1 to 3, the pharmaceutically acceptable acid addition salts thereof and, where applicable the optical, geometrical and stereoisomers and racemic mixtures thereof. The compounds of this invention display utility as analgesics, anticonvulsants, for enhancing memory and for the treatment of Alzheimer's disease.

35 Claims, No Drawings

1,3-DIHYDRO-1-(PYRIDINYLAMINO)-2H-INDOL-2-ONES

This invention relates to compounds of the formula

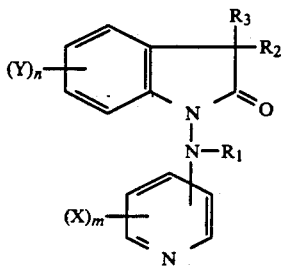

where $R_1$, $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl or heteroaryl cycloalkane; X and Y are independently hydrogen, halogen, hydroxy, loweralkyl, loweralkoxy, nitro, amino or trifluoromethyl; m and n are independently integers of 1 to 3, the pharmaceutically acceptable acid addition salts thereof and, where applicable the optical, geometrical and stereoisomers and racemic mixtures thereof. The compounds of this invention display utility as analgesics, anticonvulsants, for enhancing memory and for the treatment of Alzheimer's disease.

Preferred embodiments of the invention are those of Compound I where $R_1$ is selected from hydrogen and loweralkyl; $R_2$ is selected from hydrogen and loweralkyl; $R_3$ is selected from hydrogen and loweralkyl.

Most preferred embodiments of the invention are those of Compound I where $R_1$ is selected from loweralkyl; $R_2$ is selected from hydrogen; and $R_3$ is selected from hydrogen.

Throughout the specification and the appended claims, a given chemical formula or name shall encompass all optical, geometrical and stereoisomers thereof and racemic mixtures where such isomers and mixtures exist.

In the above definition, the term "lower" means the group it is describing contains from 1 to 6 carbon atoms. The term "alkyl" refers to a straight or branched chain hydrocarbon containing no unsaturation, e.g., methyl, ethyl, isopropyl, t-butyl, neopentyl, n-hexyl, etc.; the term "arylloweralkyl" refers to a monovalent substituent which consists of an "aryl" group e.g., phenyl, o-tolyl, m-methoxyphenyl, etc., as defined by the formula

where Z is as defined below, and m is an integer of 1 to 3, linked through a loweralkylene group having its free valance bond from a carbon of the loweralkylene group, and having a formula of

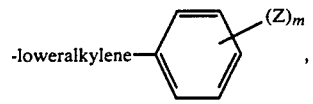

where Z is hydrogen, halogen, loweralkyl, loweralkoxy, $CF_3$, $NO_2$ and $NH_2$, OH and m is as previously defined; the term "alkylene" refers to a bivalent radical of the lower branched or unbranched alkyl group it is derived from having valence bonds from two terminal carbons thereof; e.g., ethylene ($-CH_2CH_2-$), propylene ($-CH_2CH_2CH_2-$),

etc.; the term "heteroaryl" refers to a aromatic heterocyclic mono- or bicyclic radical, e.g., pyridinyl, thiophene, etc.; and the term "heteroarylloweralkyl" refers to a loweralkyl group having a heteroaryl substituent thereon; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; and the term "halogen" refers to a member of the halogen family consisting of fluorine, chlorine, bromine and iodine.

The compounds of the present invention are prepared in the following manner. The substituents are as defined above unless indicated otherwise.

A 1-aminooxindole having the formula

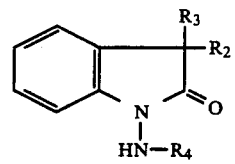

where $R_4$ is hydrogen or loweralkyl, in solution with a loweralkanol or phenolic solvent, i.e., phenol, isopropanol, butanol, etc., is reacted with an optionally substituted halopyridine hydrochloride of the formula

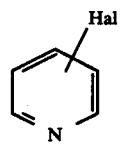

where Hal is halogen, to afford Compound I of the invention of the formula

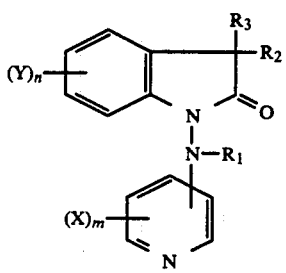

The 1-aminooxindole, Compound II, is typically synthesized utilizing procedures described in Baumgarten et al., *J. Am. Chem. Soc.* 82, 3977-82 (1960), which discloses the formation of 1-aminooxindole by the reduction of 3-cinnolinol with zinc and $H_2SO_4$ and by thermal cyclization of o-hydrazinophenylacetic acid.

Typically, the formation of Compound I is conducted under an inert atmosphere, i.e., nitrogen or argon, at a temperature of 80° C. to 150° C. for ½ to 24 hours.

To prepare Compound I where $R_1$=alkyl, 1-aminooxindole is reacted with propionaldehyde in the presence of a catalyst, i.e., p-toluenesulfonic acid to afford Compound IV of the formula

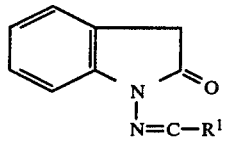

(IV)

Compound IV is in turn reduced with sodium cyanoborohydride ($NaBH_3CN$) to afford Compound V of the formula

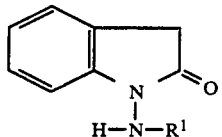

(V)

This reaction typically takes place in an lower alkanol solvent, i.e., methanol, at a temperature of 0° to 50° C. for 0.25 to 6 hours. The reduction using $NaBH_3CN$ is described in Borch et al., *J. Am. Chem. Soc.*, 93, 2897, 1971.

Compound V is reacted with a halopyridine hydrochloride i.e., 4-bromopyridine HCl or 4-chloropyridine HCl to give Compound I, where $R_1$=alkyl.

Compounds of the present invention are useful as analgesic agents due to their ability to alleviate pain in mammals. The activity of the compounds is demonstrated in the phenyl-para-quinone writhing assay in mice, a standard assay for analgesia [*Proc. Soc. Exptl. Biol. Med.*, 95, 729 (1957)]. Presented in Table 1 is the analgesic effect of some of the compounds of the invention expressed as either the subcutaneous dose at which 50% of the phenyl-para-quinone induced writhing is inhibited in the animals, i.e., the $ED_{50}$ value, or as the % decrease in writhing at a given dose.

TABLE 1

| Compound | $ED_{50}$ or % Inhibition of Writhing |
|---|---|
| 1,3-Dihydro-1-(4-pyridinyl-amino)-2H-indol-2-one | $ED_{50}$ = 0.69 mg/kg, s.c. |
| 1,3-Dihydro-1-(propyl-4-pyridinyl-amino)-2H-indol-2-one | −58% at 20 mg/kg, s.c. |
| Salicylic Acid (standard) | $ED_{50}$ = 3.28 mg/kg, s.c. |

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are examples only and that they do not, to any extent, limit the scope or practice of the invention.

The compounds of the present invention are also useful in the treatment of various memory dysfunctions characterized by decreased cholinergic function such as Alzheimer's Disease. This utility is demonstrated in the Dark Avoidance Assay.

DARK AVOIDANCE ASSAY

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chambers, the animal re-enters the dark compartment shortly after being placed in the test chamber 24 hours later. The effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Presented in Table 2 is the activity of some of the compounds of the invention in this assay.

TABLE 2

| Compound | Dose (mg/kg of body wt) | % of Animals With Scopolamine Induced Memory Deficit Reversal |
|---|---|---|
| 1,3-Dihydro-1-(4-pyridinylamino)-2-indol-2-one | 0.31 mg/kg, s.c. | 27% |
| | 0.63 | 27% |
| | 1.25 | 27% |
| 1,3-Dihydro-1-(propyl-4-pyridinylamino)-2H-indol-2-one | 1.25 mg/kg, s.c. | 27% |
| Tacrine (standard) | 0.63 | 13% |
| Pilocarpine (standard) | 1.25 | 19% |

The compounds of the invention are also useful as anticonvulsants due to their anticonvulsant activity in mammals. Anticonvulsant activity is measured in the male mouse using the supramaximal electroshock (SES) assay described in *Arch. Int. Pharmacodyn.* 92:97-107, 1952. In this procedure, groups of male mice (Charles River, CD-1, 18-30 gm) are used. Drugs are prepared using distilled water and, if insoluble, a surfactant is added. Control animals receive vehicle. Drugs are routinely administered interperitoneally (i.p.) The dosage volume is 10 ml/kg. A primary screen is given a 30 minute pretreat. The animals' eyes are placed across the output terminals of an A.C. shocker that delivers 206 volts rms for 300 msec. Electrode paste coats the animals' eyes at the point of contact with the terminals. A compound is considered to give protection if the mouse does not exhibit extensor tonus. Protection is expressed as normalized percent inhibition relative to vehicle control.

The anticonvulsant activity of one of the compounds is given below.

| Compound | ED$_{50}$ mg/kg i.p. |
|---|---|
| 1,3-Dihydro-1-(propyl-4-pyridinyl-amino)-2H-indol-2-one | 15.9 |
| Phenobarbital (standard) | 8.4 |

Effective amounts of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ®, corn starch and the like; a lubricant such as magnesium strearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:

1,3-Dihydro-1-[ethyl-(3-nitro-4-pyridinyl)amino]-3,3-dimethyl-2H-indol-2-one;

1,3-Dihydro-1-[(3-fluoro-4-pyridinyl)propylamino]-2H-indol-2-one;

1,3-Dihydro-3-methyl-1-(4-pyridinylamino)-2H-indol-2-one;

1,3-Dihydro-3,3-dimethyl-1-(methyl-4-pyridinylamino)-2H-indol-2-one;

1,3-Dihydro-6-methyl-1-(4-pyridinylamino)-2H-indol-2-one;

1-[(3-Amino-4-pyridinyl)butylamino]-1,3-dihydro-3-methyl-2H-indol-2-one;

1,3-Dihydro-1-[(3-methyl-4-pyridinyl)propylamino]-3-phenylmethyl-2H-indol-2-one;

3,3-Diethyl-1,3-dihydro-1-[(3-ethyl-4-pyridinyl)amino]-2-H-indol-2-one;

1,3-Dihydro-1-[(3-fluoro-4-pyridinyl)-1-(2-propenyl)amino]-2H-indol-2-one;

1,3-Dihydro-3-methyl-1-[(3-methyl-4-pyridinyl)-1-(2-propynyl)-amino]-2H-indol-2-one;

1,3-Dihydro-1-[(3-phenylmethyl-4-pyridinyl)amino]-2H-indol-2-one;

1-[(3-Amino-4-pyridinyl)methylamino]-1,3-dihydro-3-propyl-2H-indol-2-one;

1,3-Dihydro-1-(propyl-3-pyridinylamino)-2H-indol-2-one;

1-[(4-Amino-3-pyridinyl)methylamino]-1,3-dihydro-3-propyl-2H-indol-2-one;

1-[(4-Fluoro-3-pyridinyl)propylamino]-1,3-dihydro-2H-indol-2-one;

1,3-Dihydro-1'-(4-pyridinylamino)spiro[2H-indene-2,3'-[3H]indol]-2'(1'H)-one.

The following examples are for illustrative purposes only and are not to be construed as limiting the invention. All temperatures are given in degrees centigrade (° C.) unless otherwise designated.

EXAMPLE 1

1,3-Dihydro-1-(propyl-4-pyridinylamino)-2H-indol-2-one

To a stirred solution of 1-(propylamino)-oxindole (10.4 g) and phenol (30.8 g), preheated to 150° C. under nitrogen, was added 4-bromopyridine hydrochloride (11.04 g) over 5 min. Heating was continued for 7 hours at which time the reaction mixture was cooled to room temperature and made basic by slow addition of dilute aqueous sodium hydroxide. The product was extracted four times with ethyl acetate and the combined organic layers back-extracted with dilute aqueous sodium hydroxide, washed with brine, and dried ($K_2CO_3$). Filtration and concentration gave the crude product. Purification via flash column chromatography (silica gel, EtOAc), preparative high performance liquid chromatography (HPLC) (silica gel, EtOAc→2% $Et_3N$/0–7% MeOH/EtOAc), and a third column (alumina, EtOAc) followed. Recrystallization from ethyl acetate-pentane afforded 2.10 g (14%) of 1,3-dihydro-1-(propyl-4-pyridinylamino)-2H-indol-2-one, as a solid, m.p. 140°–143° C.

Analysis: Calculated for $C_{16}H_{17}N_3O$: 71.89% C, 6.41% H, 15.72% N. Found: 71.69% C, 6.40% H, 15.64% N.

EXAMPLE 2

1,3-Dihydro-1-(4-pyridinylamino)-2H-indol-2-one

To a stirred solution of 1-aminooxindole (10.0 g) and isopropanol (270 ml) was added 4-chloropyridine hydrochloride (15.21 g). The flask was fitted with a condensor and nitrogen inlet and flushed with nitrogen. The reaction mixture was heated at reflux for 15½ hours. Upon cooling to room temperature, saturated aqueous sodium bicarbonate was added to neutralize the hydrochloride salts. Solid sodium bicarbonate was added until gas evolution ceased. The resulting slurry was mixed with methanol-dichloromethane and filtered. The solids were washed with methanol-dichloromethane and the combined filtrate concentrated. Purification via flash column chromatography (silica gel, 2% $Et_3N$/0→10% MeOH/EtOAc) afforded fractions from which the product crystallized. The mother liquor was concentrated and a second crop of product was obtained. Obtained was 4.81 g (31%) of 1,3-dihydro-1-(4-pyridinylamino)-2H-indol-2-one, as a solid, m.p. 221°–224° C.

Analysis: Calculated for $C_{13}H_{11}N_3O$: 69.32% C, 4.92% H, 18.65% N. Found: 69.20% C, 4.91% H, 18.64% N.

EXAMPLE 3

1,3-Dihydro-1-(3-fluoro-4-pyridinyl amino)-2H-indol-2-one

To a stirred solution of 1-aminooxindole (10.03 g) in isopropanol (270 ml) was added 4-chloro-3-fluoropyridine hydrochloride (10.0 g). The flask was flushed with nitrogen and fitted with a reflux condensor and nitrogen inlet. The reaction mixture was heated at reflux for 22 hours. Upon cooling to room temperature, the reaction mixture was poured into dilute aqueous sodium bicarbonate and ethyl acetate. The layers were separated and the aqueous layer extracted twice with ethyl acetate and once with ether. The combined organic layers were washed with brine and dried ($K_2CO_3$). Filtration and concentration gave the crude product.

Purification via preparative high pressure liquid chromatography (HPLC) (silica gel, 3% MeOH/DCM) followed by trituration with ether-pentane afforded 4.4 g (30%) of 1,3-Dihydro-1-(3-fluoro-4-pyridinylamino)-2H-indol-2-one as a solid, m.p. 181°–183° C.

Analysis: Calculated for $C_{13}H_{10}FN_3O$: 64.19% C, 4.14% H, 17.27% N. Found: 64.10% C, 4.09% H, 17.25% N.

EXAMPLE 4

1,3-Dihydro-3,3-dimethyl-1-(propyl-4-pyridinylamino)-2H-indol-2-one

To a stirred solution of 1-amino-3,3-dimethyloxindole (7.35 g) and isopropanol (167 ml) was added 4-chloropyridine hydrochloride (8.15 g). The flask was flushed with nitrogen and fitted with a condensor and nitrogen inlet. The reaction mixture was heated at reflux for 9 hours. Upon cooling to room temperature, the reaction mixture was poured into dilute aqueous sodium bicarbonate. The product was extracted thrice with ethyl acetate and once with dichloromethane. The combined organic layers were washed with brine and dried ($K_2CO_3$). Filtration and concentration gave the crude product. Purification via flash column chromatography (silica gel, 2% $Et_3N$/0–2% MeOH/ether) afforded 3.5 g (33%) of the desired product.

To a solution consisting of the above product (3.36 g) and dimethylformamide (120 ml), cooled to 0° C. under nitrogen, was added sodium hydride (0.36 g). Stirring was continued at 0° C. for 35 min at which time bromopropane (1.3 ml) was added dropwise. The reaction mixture was allowed to slowly warm over 1½ hours, then poured into ethyl acetate and water. The layers were separated and the aqueous layer extracted with ethyl acetate. The combined organic layers were back-washed with water, brine, and dried ($K_2CO_3$). Filtration and concentration gave the crude product. Purification via flash column chromatography (silica gel, 2% $Et_3N$/0–1% MeOH/ether) afforded 3.5 g (87%) of 1,3-dihydro-3,3-dimethyl-1-(propyl-4-pyridinylamino)-2H-indol-2-one, m.p. 125°–127° C.

Analysis: Calculated for $C_{18}H_{21}N_3O$: 73.19% C, 7.17% H, 14.23% N. Found: 73.33% C, 7.20% H, 14.20% N.

We claim:

1. A 1,3-dihydro-1-(pyridinylamino)-2H-indol-2-one of the formula

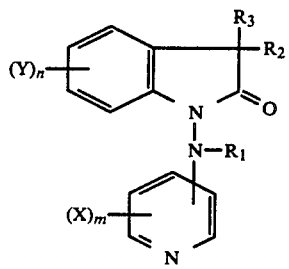

where $R_1$ is hydrogen, loweralkyl, aryl, arylloweralkyl or heteroarylloweralkyl selected from the group consisting of pyridinylmethyl, pyridinylethyl, thienylmethyl, thienylethyl; $R_2$ and $R_3$ are independently hydrogen, loweralkyl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro fused arylcycloalkane, spiro fused pyridinylcycloalkane or spiro fused thiophenylcycloalkane, X and Y are independently hydrogen, halogen, hydroxy, loweralkyl, loweralkoxy, nitro, amino or trifluoromethyl; m and n are independently integers of 1 to 3, or the pharmaceutically acceptable acid addition salts thereof or, where applicable, the optical, geometrical or stereoisomers or racemic mixtures thereof.

2. A compound as defined in claim 1 wherein $R_1$, $R_2$ and $R_3$ are independently hydrogen or loweralkyl.

3. A compound as defined in claim 2 wherein $R_1$ is loweralkyl and $R_2$ and $R_3$ are independently hydrogen or loweralkyl.

4. A compound as defined in claim 3 wherein $R_1$, $R_2$ and $R_3$ are loweralkyl.

5. The compound as defined in claim 3 which is 1,3-dihydro-1-(propyl-4-pyridinylamino)-2H-indol-2-one.

6. The compound as defined in claim 2 which is 1,3-dihydro-1-(4-pyridinylamino)-2H-indol-2-one.

7. The compound as defined in claim 2 which is 1,3-dihydro-1-(3-fluoro-4-pyridinylamino)-2H-indol-2-one.

8. The compound as defined in claim 4 which is 1,3-dihydro-3,3-dimethyl-1-(propyl-4-pyridinylamino)-2H-indol-2-one.

9. An analgesic composition which comprises an effective pain alleviating amount of a compound as defined in claim 1 and a suitable carrier therefor.

10. A composition as defined in claim 9 wherein $R_1$, $R_2$ and $R_3$ are independently hydrogen or loweralkyl.

11. A composition as defined in claim 10 wherein $R_1$ is loweralkyl and $R_2$ and $R_3$ are independently hydrogen or loweralkyl.

12. A composition as defined in claim 11 wherein $R_1$, $R_2$ and $R_3$ are loweralkyl.

13. The composition as defined in claim 11 which comprises 1,3-dihydro-1-(propyl-4-pyridinylamino)-2H-indol-2-one.

14. The composition as defined in claim 10 which comprises 1,3-dihydro-1-(4-pyridinylamino)-2H-indol-2-one.

15. The composition as defined in claim 10 which comprises 1,3-dihydro-1-(3-fluoro-4-pyridinylamino)-2H-indol-2-one.

16. The composition as defined in claim 12 which comprises 1,3-dihydro-3,3-dimethyl-1-(propyl-4-pyridinylamino)-2H-indol-2-one.

17. An anticonvulsant pharmaceutical composition which comprises an anticonvulsant effective amount of a compound as defined in claim 1 and a suitable carrier therefor.

18. A composition as defined in claim 17 wherein $R_1$, $R_2$ and $R_3$ are independently hydrogen or loweralkyl.

19. A composition as defined in claim 18 wherein $R_1$ is loweralkyl and $R_2$ and $R_3$ are independently hydrogen or loweralkyl.

20. A composition as defined in claim 19 wherein $R_1$, $R_2$ and $R_3$ are loweralkyl.

21. The composition as defined in claim 19 which comprises 1,3-dihydro-1-(propyl-4-pyridinylamino)-2H-indol-2-one.

22. The composition as defined in claim 18 which comprises 1,3-dihydro-1-(4-pyridinylamino)-2H-indol-2-one.

23. The composition as defined in claim 18 which comprises 1,3-dihydro-1-(3-fluoro-4-pyridinylamino)-2H-indol-2-one.

24. The composition as defined in claim 20 which comprises 1,3-dihydro-3,3-dimethyl-1-(propyl-4-pyridinylamino)-2H-indol-2-one.

25. A pharmaceutical composition for enhancing memory which comprises an effective memory enhancing amount of a compound as defined in claim 1 and a suitable carrier therefor.

26. A composition as defined in claim 25 wherein $R_1$, $R_2$ and $R_3$ are independently hydrogen or loweralkyl.

27. A composition as defined in claim 26 wherein $R_1$ is loweralkyl and $R_2$ and $R_3$ are independently hydrogen or loweralkyl.

28. A composition as defined in claim 27 wherein $R_1$, $R_2$ and $R_3$ are loweralkyl.

29. The composition as defined in claim 27 which comprises 1,3-dihydro-1-(propyl-4-pyridinylamino)-2H-indol-2-one.

30. The composition as defined in claim 26 which comprises 1,3-dihydro-1-(4-pyridinylamino)-2H-indol-2-one.

31. The composition as defined in claim 26 which comprises 1,3-dihydro-1-(3-fluoro-4-pyridinylamino)-2H-indol-2-one.

32. The composition as defined in claim 28 which comprises 1,3-dihydro-3,3-dimethyl-1-(propyl-4-pyridinylamino)-2H-indol-2-one.

33. A method of alleviating pain in a mammal which comprises administering to a mammal a pain alleviating effective amount of a compound as defined in claim 1.

34. A method of treating convulsions in a mammal which comprises administering to a mammal an anticonvulsant effective amount of a compound as defined in claim 1.

35. A method of treating a mammal in need of memory enhancement which comprises administering to a mammal a memory enhancing effective amount of a compound as defined in claim 1.

* * * * *